(12) United States Patent
Ito et al.

(10) Patent No.: US 8,969,523 B2
(45) Date of Patent: Mar. 3, 2015

(54) SEBUM SECRETION-BLOCKING COMPOSITION, AND FOOD OR BEVERAGE CONTAINING SAME

(71) Applicant: Lotte Co., Ltd., Tokyo (JP)

(72) Inventors: Masanori Ito, Sayama (JP); Masayuki Yugi, Nakano-ku (JP); Katsumasa Shimizu, Nakano-ku (JP); Chiharu Takamatsu, Saitama (JP); Eriko Otani, Saitama (JP); Takaya Hashizume, Shinjuku-ku (JP)

(73) Assignee: Lotte Co., Ltd., Tokyo (JP)

( * ) Notice: Subject to any disclaimer, the term of this patent is extended or adjusted under 35 U.S.C. 154(b) by 0 days.

(21) Appl. No.: 13/935,620

(22) Filed: Jul. 5, 2013

(65) Prior Publication Data

US 2013/0296533 A1 Nov. 7, 2013

Related U.S. Application Data

(62) Division of application No. 13/519,581, filed as application No. PCT/JP2010/007370 on Dec. 20, 2010.

(30) Foreign Application Priority Data

Dec. 28, 2009 (JP) ................................. 2009-297848

(51) Int. Cl.
| | |
|---|---|
| *A61K 38/39* | (2006.01) |
| *A23G 1/32* | (2006.01) |
| *A23G 1/44* | (2006.01) |
| *A23G 3/36* | (2006.01) |
| *A23G 3/44* | (2006.01) |
| *A23G 4/06* | (2006.01) |
| *A23G 4/14* | (2006.01) |
| *A23G 9/32* | (2006.01) |
| *A23G 9/38* | (2006.01) |
| *A23J 3/34* | (2006.01) |
| *A23L 1/305* | (2006.01) |
| *A23L 1/308* | (2006.01) |
| *A23L 2/52* | (2006.01) |
| *A23L 2/66* | (2006.01) |
| *A61K 38/01* | (2006.01) |

(52) U.S. Cl.
CPC . *A61K 38/39* (2013.01); *A23G 1/32* (2013.01); *A23G 1/44* (2013.01); *A23G 3/36* (2013.01); *A23G 3/44* (2013.01); *A23G 4/06* (2013.01); *A23G 4/14* (2013.01); *A23G 9/32* (2013.01); *A23G 9/38* (2013.01); *A23J 3/342* (2013.01); *A23L 1/3053* (2013.01); *A23L 1/3085* (2013.01); *A23L 2/52* (2013.01); *A23L 2/66* (2013.01); *A61K 38/014* (2013.01); *A23V 2002/00* (2013.01)
USPC ....................................................... 530/356

(58) Field of Classification Search
CPC . A61K 38/39; A61K 38/014; A23V 2002/00; A23V 2250/5422; A23J 3/342; A23L 1/3053; A23L 1/3085
USPC ......................................................... 530/356
See application file for complete search history.

(56) References Cited

U.S. PATENT DOCUMENTS

| | | | | |
|---|---|---|---|---|
| 5,071,960 | A | * 12/1991 | Turowski et al. | ............. 530/356 |
| 2005/0266137 | A1 | 12/2005 | Eppler et al. | |
| 2006/0275345 | A1 | 12/2006 | Butzengeiger et al. | |
| 2008/0299159 | A1 | 12/2008 | Aimi et al. | |
| 2011/0039767 | A1 | 2/2011 | Nieuwenhuizen et al. | |

FOREIGN PATENT DOCUMENTS

| | | | |
|---|---|---|---|
| JP | 03-220129 | A | 9/1991 |
| JP | 07-278012 | A | 10/1995 |
| JP | 11-308977 | A | 11/1999 |
| JP | 2000-093121 | A | 4/2000 |
| JP | 2002-255847 | A | 9/2002 |
| JP | 2007-099751 | A | 4/2007 |
| JP | 2007-320891 | A | 12/2007 |
| JP | 2008-509905 | A | 4/2008 |
| JP | 2008-194010 | A | 8/2008 |
| JP | 2008-297241 | A | 12/2008 |
| WO | WO 2006/016728 | A1 | 2/2006 |

OTHER PUBLICATIONS

Definition of derivative from http://cancerweb.ncl.ac.uk/omd/about. html, pp. 1-5. Accessed Jul. 7, 2005.*
Liduan, Yin et al., "Application of collagen hydrolysate in the fields of functional foods and cosmetics," Agricultural Engineering Technology, vol. 10, Dec. 31, 2007.
Office Action dated Aug. 15, 2013, in Chinese Patent Application No. 201080059485.1.
Taikai Koen Yoshishu, The Japanese Society of Nutrition and Food Science, Apr. 1, 2006, 60$^{th}$, pp. 370, 3J-4a.
International Preliminary Report on Patentability for International Patent Application No. PCT/JP2010/007370, Jul. 4, 2012.
"Don't Forget to Moisture When Doing Oil Control," Oak International Health Organization, Skin Care Tips 101, pp. 66-67, Oct. 31, 2008.

(Continued)

*Primary Examiner* — Julie Ha
(74) *Attorney, Agent, or Firm* — Miles & Stockbridge P.C.

(57) ABSTRACT

An object is to provide a sebum secretion inhibiting composition and a food or drink product using the same. The present inventors have conducted extensive studies and consequently found that the sebum secretion is inhibited by orally ingesting a collagen peptide, which is hydrolyzed collagen, and provide an oral sebum secretion inhibiting composition comprising a collagen hydrolysate and a food or drink product containing the composition.

12 Claims, 1 Drawing Sheet

(56) References Cited

OTHER PUBLICATIONS

Office Action dated May 4, 2014, in Chinese Patent Application No. 201080059485.1.

Office Action issued Sep. 25, 2014, in Japanese Patent Application No. 2009-297848.

* cited by examiner

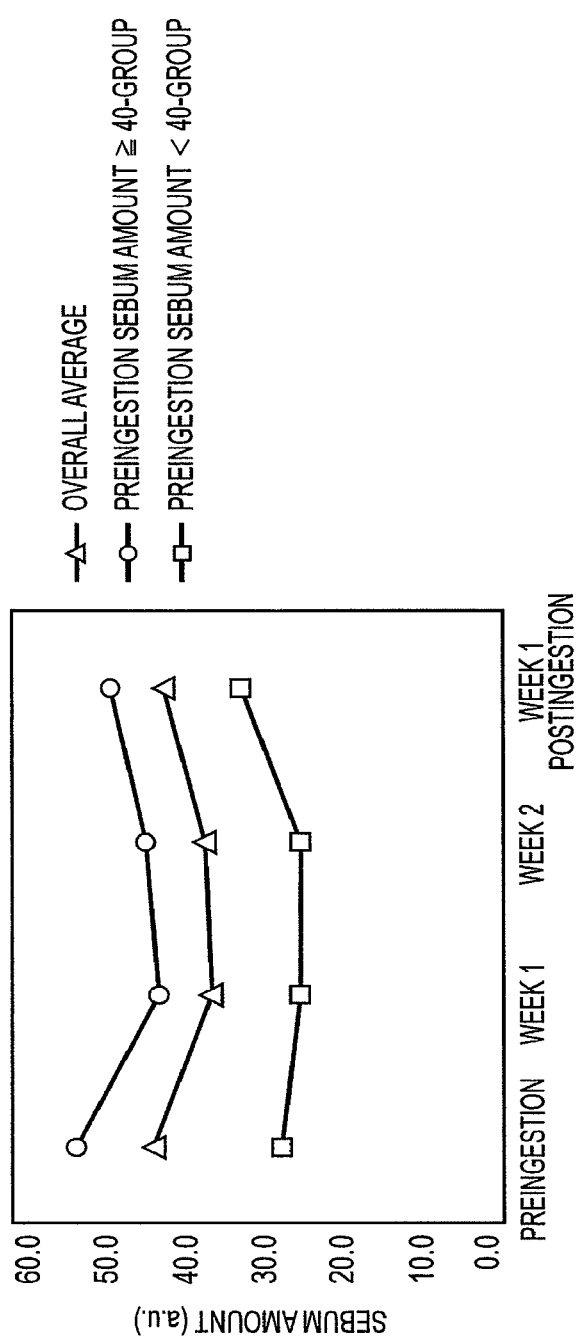

8,969,523 B2

SEBUM SECRETION-BLOCKING COMPOSITION, AND FOOD OR BEVERAGE CONTAINING SAME

TECHNICAL FIELD

The present invention relates to a sebum secretion inhibitor (blocker) and a food or drink product and a composition using the same.

BACKGROUND ART

Sebum refers to lipid found in the human epidermis and is a mixture of a sebaceous secretion and the lipids derived from the epidermis, comprising triglycerides, fatty acids, wax esters, etc. In the human epidermis, 0.05 to 0.4 $mg/cm^2$ of sebum is considered to be always present. Sebum moisturizes and softens the stratum corneum and also prevents external harmful substances and bacteria from invading and prevents substances such as water from being released out of the body. The amount of sebum varies depending on sites of the body, age, sex, the season, temperature, fat intake, etc. Generally, in humans, the sebum amount is known to be greater in men than in women, and is further abundant in fetuses and newborns, adolescents, and middle-aged to elderly men.

The sebum amount is an important factor to determine the skin type. The skin with a large amount of sebum is classified as oily skin, whereas the skin with a small amount of sebum is classified as not oily skin. When the oiliness increases, the skin becomes greasy, which gives an unpleasant feeling not only to the person him or herself but also to others. Also, when a sebum amount is excessive, sebum accumulates together with the stratum corneum inside the pores and may induce acne.

Accordingly, there is a need for a sebum secretion inhibitor which inhibits the sebum secretion. Although there are a variety of topical sebum secretion inhibitors, inhibition by an external medicine often fails to provide a fundamental solution, and there is a need for an orally administrable sebum secretion inhibitor. The orally administrable sebum secretion inhibitor is desirably comprising ingredients derived from food products or natural products to assure safety. Thus, the present invention provides a sebum secretion inhibitor comprising a collagen degradation product.

The following products are reported as orally administrable compositions for fine skin comprising food products or ingredients derived from natural products. Patent Literature 1 discloses a composition for fine skin and a hair growth formula containing as an active ingredient a polar solvent extract of kiwi fruit seeds. However, Patent Literature 1 does not mention the relationship between the active ingredient and the sebum secretion inhibition. Further, Patent Literature 2 discloses a preventive and therapeutic composition for psilosis and seborrheic skin diseases containing the extract of kiwi fruit. However, Patent Literature 2 mainly describes inhibition of psilosis and does not discuss the sebum secretion inhibitory effect in detail.

The following compositions are reported as orally administrable compositions for fine skin associated with collagen or degradation products thereof. More specifically, Patent Literature 3 discloses a composition for fine skin containing ingredients such as collagen, hyaluronic acid, etc., obtained by digesting skin of birds, etc., with protease, or the like. Patent Literature 4 discloses an orally administrable composition for promoting fine skin comprising collagen, and the like, and other substances. Patent Literature 5 discloses a composition containing a collagen hydrolysate. However, none of these literatures suggests or discloses the relation between collagen or a collagen degradation product and the sebum secretion inhibition.

CITATION LIST

Patent Literature

PTL 1: Japanese Patent Application Laid-Open No. 2007-99751
PTL 2: Japanese National Publication of International Patent Application No. 2008-509905
PTL 3: Japanese Patent Application Laid-Open No. H11-308977
PTL 4: Japanese Patent Application Laid-Open No. 2007-320891
PTL 5: Japanese Patent Application Laid-Open No. 2008-194010

SUMMARY OF INVENTION

Technical Problem

An object is to provide a sebum secretion inhibitor and a food or drink product and a composition using the same.

Solution to Problem

The present inventors have conducted extensive studies and consequently found that the sebum secretion is inhibited by orally ingesting a collagen peptide, which is hydrolyzed collagen, whereby the present invention has been accomplished. More specifically, the present invention provides an oral sebum secretion inhibiting composition comprising a collagen hydrolysate and a food or drink product containing the composition.

Advantageous Effects of Invention

Collagen accounts for high percentage in the total protein in vivo in the mammals and can be obtained at a low cost. Collagen is also a raw material for a gelatin and glue and has long been used as a food material. Collagen is further ingested in everyday life from a meat stew, etc., and thus its safety is widely acknowledged.

Furthermore, the sebum secretion inhibitor of the present invention provides the significant sebum secretion inhibitory effect in a short period of time.

BRIEF DESCRIPTION OF DRAWINGS

FIG. 1 is a graph showing the sebum amounts of the subjects before, during and after the ingestion of the powder test meal.

DESCRIPTION OF EMBODIMENTS

Hereinafter, the orally administrable sebum secretion inhibiting composition comprising a collagen hydrolysate of the present invention and the food or drink product containing the composition are described.

Collagen is a main protein component constituting connective tissue in animals and is characterized by having a collagen triple helical structure. A total of not less than 30 types of collagen have been reported which are respectively termed Type I, Type II, and so on. Type I collagen is the primary component of the derma, ligaments, tendons, bones and the like; and Type II collagen is the primary component of articular cartilage. Further, Type IV collagen is mainly contained in a basal membrane, which is the undercoat of all epithelial tissues. Type I collagen is the most abundant collagen in the body.

In the sebum secretion inhibiting composition of the present invention, the collagen origin is not limited, and usable are those derived from mammals such as cow, pig, etc., birds such as chicken, ostrich, etc., fishes such as sharks, etc. Those derived from livestock such as cow, pig, chicken, etc., are easily obtainable in a large amount, hence particularly preferable. Further, the type of collagen is not limited and any type can be used, or a plurality of collagen types may be used in mixture.

In the present invention, the collagen hydrolysate (hereinafter sometimes referred to as collagen peptide) refers to a low molecular collagen obtained by hydrolyzing collagen with an acid, alkali or enzyme. For example, a collagen hydrolysate can be obtained by immersing skins and joints of animals such as pig, cow and chicken or scales and skins of fish in an acid or alkali solution to extract gelatin and treating the extracted gelatin with an enzyme or acid. The gelatin refers to the collagen pre-treated with an acid or alkali and then solubilized by heat hydrolysis.

The sebum secretion inhibiting composition of the present invention is for oral administration, but the dosage form is not limited and can be administered in the form of, for example, tablets, capsules, drinks, etc. Further, the sebum secretion inhibiting composition of the present invention may be administered by being contained in a food or drink product, and, in that case, the food or drink product in which the composition is contained are not limited, and examples include carbonated drinks, nutritional drinks, liquors, sweets, nutritional food products, frozen sweets, dairy products, meats, etc., and food products as a raw material to be used for these products.

The sebum secretion inhibiting composition of the present invention refers to a composition which inhibits sebum secreted from skin and the skin may be derived from any site of the body, but face, head, chest, back, armpits, genital area, etc., known as the areas where sebaceous glands are dense have abundant sebum secretion, hence are included as target sites.

EXAMPLE

Hereinafter, the present invention will be described in detail with reference to Examples. However, the present invention is not limited to the following Examples.

Example 1

For the collagen hydrolysate, a commercial "Collagen Peptide" (pig) having a molecular weight of 20000 or less was used. The collagen peptide used was obtained by immersing the pig skin in an acid or alkali solution to extract gelatin and further enzymolyzing the extracted gelatin. The collagen peptide is mainly derived from pig Type I collagen.

For the test meal containing the collagen peptide, a powder test meal comprising the composition shown in Table 1 was prepared. The powder test meal contains 10000 mg of collagen peptide and 100 mg of vitamin C per meal. Vitamin C is added because it is required to synthesize collagen in vivo.

TABLE 1

| Ingredient name | g/meal |
| --- | --- |
| Collagen peptide | 10.0 |
| Excipient, sweetener | 1.7 |
| Flavor | 0.2 |
| Vitamin C | 0.1 |
| Total | 12.0 |

Sixteen men in their twenties and thirties as the subjects orally ingested the powder test meal. The subjects took one meal of the powder test meal added to milk, juice, miso soup or the like at any convenient time once a day for 12 consecutive days. The sebum amount of the subjects was measured before, during and after the ingestion of the powder test meal. On the measurement day, the subjects washed their faces with warm water and a facial soap at 1 p.m., and 2 hours later, i.e., around 3 p.m., the measurement was carried out. The measurement was carried out, using an optical sebum measurement apparatus, Triplesense (Moritex Precision Corporation), by pressing the sensor part of the measurement apparatus against a spot about 3 cm below the eye on the face of the subject. The value (arbitrary unit a.u.) indicated as an oil content measurement value by the measurement apparatus was referred to as the sebum value. Before ingesting the powder test meal, 10 of the subjects had a sebum amount of 40 a.u. or more, whereas 6 subjects had a sebum amount of below 40 a.u. These groups were termed as the preingestion sebum amount≥the 40-group and the preingestion sebum amount<the 40-group, respectively. Table 2 shows the average value of the sebum amount of all subjects, the average value of the sebum amount of the preingestion sebum amount≥the 40-group and the average value of the sebum amount of the preingestion sebum amount<the 40-group before ingesting the powder test meal, 1 week and 2 weeks after the start of ingestion and 1 week after the completion of ingestion. Similarly, the results in the form of graph are shown in FIG. 1. In FIG. 1, Δ represents the average value for all subjects, ○ represents the average value of the sebum amount of the preingestion sebum amount≥the 40-group, and □ represents the average value of the sebum amount of the preingestion sebum amount<the 40-group.

TABLE 2

|  | Preingestion (a.u.) | Week 1 (a.u.) | Week 2 (a.u.) | Postingestion Week 1 (a.u.) |
| --- | --- | --- | --- | --- |
| Overall average | 42.6 | 35.4 | 36.3 | 41.3 |
| Preingestion sebum amount ≥ 40-group | 52.1 | 41.9 | 43.4 | 47.6 |
| Preingestion sebum amount < 40-group | 26.9 | 24.7 | 24.4 | 31.8 |

After ingesting the powder test meal, all groups had reduced sebum amounts in comparison with before ingestion which revealed that the sebum secretion was inhibited owing to the ingestion of the powder test meal. In particular, the sebum secretion inhibitory effect was significant in the preingestion sebum amount≥the 40-group which leads to the presumption that people with oily skin inherently are most likely to benefit the effect. The effect already started showing within 1 week after the ingestion and the sebum amount increased again 1 week later from the ingestion which leads to the presumption that the effect can be attained in a comparatively short period of time.

The same test was also carried out for the group which did not ingest the powder test meal but the sebum inhibitory effect was not observed.

Examples of application of the deodorized collagen peptide obtained based on the above test results to drink or food products or compositions, are shown below.

Using the present product (collagen peptide) prepared by the methods described in Example 1, a drink, a powder, a tablet, a chewing gum, a candy, a tablet candy, a gummy jelly, a chocolate and a sorbet were produced with the following formula.

Example 2

Formula for a Drink

| | |
|---|---|
| Collagen peptide | 5.0 parts by weight |
| High fructose corn syrup | 8.0 parts by weight |
| Sugar | 4.0 parts by weight |
| Flavor | 0.5 parts by weight |
| Vitamin C | 0.5 parts by weight |

After adjusting pH to 3.8 using an acidifier, the drink was prepared to be 100 parts by volume with purified water.

Example 3

Formula for a Drink

| | |
|---|---|
| Collagen peptide | 5.0 parts by weight |
| Sucralose | 0.005 parts by weight |
| Stevioside | 0.008 parts by weight |
| Rebaudioside | 0.008 parts by weight |
| Acesulfame potassium | 0.01 parts by weight |
| Peach flavor | 0.5 parts by weight |
| Vitamin C | 0.5 parts by weight |

After adjusting pH to 3.8 using an acidifier, the drink was prepared to be 100 parts by volume with purified water.

Example 4

Formula for a Drink

| | |
|---|---|
| Collagen peptide | 5.0 parts by weight |
| Acidic lactic beverage | 5.0 parts by weight |
| High fructose corn syrup | 10.0 parts by weight |
| Flavor | 0.5 parts by weight |
| Vitamin C | 0.5 parts by weight |

After adjusting pH to 3.8 using an acidifier, the drink was prepared to be 100 parts by volume with purified water.

Example 5

Formula for a Drink

| | |
|---|---|
| Collagen peptide | 5.0 parts by weight |
| High fructose corn syrup | 10.0 parts by weight |
| Honey | 5.0 parts by weight |
| Flavor | 0.5 parts by weight |
| Vitamin C | 0.5 parts by weight |

After adjusting pH to 3.8 using an acidifier, the drink was prepared to be 100 parts by volume with purified water.

Example 6

Formula for a Jelly Drink

| | |
|---|---|
| Collagen peptide | 5.0 parts by weight |
| Sucralose | 0.005 parts by weight |
| Stevioside | 0.008 parts by weight |
| Rebaudioside | 0.008 parts by weight |
| Acesulfame potassium | 0.01 parts by weight |
| Peach flavor | 0.5 parts by weight |
| Vitamin C | 0.5 parts by weight |
| Gelation stabilizer | 0.5 parts by weight |

After adjusting pH to 3.8 using an acidifier, the drink was prepared to be 100 parts by volume with purified water.

Example 7

Formula for a Jelly Drink

| | |
|---|---|
| Collagen peptide | 5.0 parts by weight |
| High fructose corn syrup | 8.0 parts by weight |
| Sugar | 4.0 parts by weight |
| Flavor | 0.5 parts by weight |
| Vitamin C | 0.5 parts by weight |
| Gelation stabilizer | 0.5 parts by weight |

After adjusting pH to 3.8 using an acidifier, the drink was prepared to be 100 parts by volume with purified water.

Example 8

Formula for a Coffee Drink

| | |
|---|---|
| Collagen peptide | 5.0 parts by weight |
| Coffee extract | 5.0 parts by weight |
| Sugar | 4.0 parts by weight |
| Flavor | 0.5 parts by weight |
| Vitamin C | 0.5 parts by weight |

After adjusting pH to 6.5 using sodium bicarbonate, the drink was prepared to be 100 parts by volume with purified water.

Example 9

Formula for a Green Tea Drink

| | |
|---|---|
| Collagen peptide | 5.0 parts by weight |
| Green tea extract | 10.0 parts by weight |
| Flavor | 0.5 parts by weight |
| Vitamin C | 0.5 parts by weight |

After adjusting pH to 6.5 using sodium bicarbonate, the drink was prepared to be 100 parts by volume with purified water.

Example 10

Formula for a Powder

| | |
|---|---|
| Collagen peptide | 90.0 parts by weight |
| Lactose | 5.0 parts by weight |
| Dextrin | 4.0 parts by weight |
| Vitamin C | 0.9 parts by weight |

Example 11

Formula for a Tablet

| | | |
|---|---|---|
| Collagen peptide | 5.0 | parts by weight |
| D-mannitol | 40.0 | parts by weight |
| Lactose | 40.0 | parts by weight |
| Crystalline cellulose | 10.0 | parts by weight |
| Vitamin C | 0.05 | parts by weight |
| Hydroxypropylcellulose | 5.0 | parts by weight |

Example 12

Formula for a Chewing Gum

| | | |
|---|---|---|
| Collagen peptide | 5.0 | parts by weight |
| Gum base | 20.0 | parts by weight |
| Sugar | 55.0 | parts by weight |
| Glucose | 10.5 | parts by weight |
| Starch syrup | 9.0 | parts by weight |
| Vitamin C | 0.05 | parts by weight |
| Flavor | 0.5 | parts by weight |

Example 13

Formula for a Candy

| | | |
|---|---|---|
| Collagen peptide | 5.0 | parts by weight |
| Sugar | 50.0 | parts by weight |
| Starch syrup | 29.5 | parts by weight |
| Flavor | 0.5 | parts by weight |
| Vitamin C | 0.05 | parts by weight |
| Water | 15.0 | parts by weight |

Example 14

Formula for a Tablet Candy

| | | |
|---|---|---|
| Collagen peptide | 5.0 | parts by weight |
| Sugar | 73.5 | parts by weight |
| Glucose | 17.0 | parts by weight |
| Sucrose esters of fatty acids | 0.2 | parts by weight |
| Flavor | 0.2 | parts by weight |
| Vitamin C | 0.05 | parts by weight |
| Water | 4.1 | parts by weight |

Example 15

Formula for a Gummy Jelly

| | | |
|---|---|---|
| Collagen peptide | 5.0 | parts by weight |
| Gelatin | 55.0 | parts by weight |
| Starch syrup | 23.0 | parts by weight |
| Sugar | 8.5 | parts by weight |
| Vegetable oil and fat | 4.5 | parts by weight |
| Mannitol | 3.0 | parts by weight |
| Vitamin C | 0.05 | parts by weight |
| Lemon juice | 1.0 | parts by weight |

Example 16

Formula for a Chocolate

| | | |
|---|---|---|
| Collagen peptide | 5.0 | parts by weight |
| Powder sugar | 36.8 | parts by weight |
| Cacao bitter | 20.0 | parts by weight |
| Whole milk powder | 20.0 | parts by weight |
| Cacao butter | 17.0 | parts by weight |
| Mannitol | 1.0 | parts by weight |
| Vitamin C | 0.05 | parts by weight |
| Flavor | 0.2 | parts by weight |

Example 17

Formula for a Sorbet

| | | |
|---|---|---|
| Collagen peptide | 5.0 | parts by weight |
| Orange juice | 25.0 | parts by weight |
| Sugar | 23.0 | parts by weight |
| Egg white | 9.0 | parts by weight |
| Vitamin C | 0.05 | parts by weight |
| Water | 38.0 | parts by weight |

Hereinabove, the present invention has been described with reference to Examples but can be carried out without being limited to these embodiments of the present invention.

This application claims the priority to the Japanese Patent Application No. 2009-297848, filed on Dec. 28, 2009, and the contents of which is hereby incorporated by reference as a part of the present application.

The invention claimed is:

1. A method for inhibiting secretion of undesirable sebum in a human, comprising oral administration to a human experiencing excessive secretion of sebum of amount of a collagen hydrolysate effective to decrease secretion of sebum.

2. The method of claim 1, wherein said oral administration is conducted by administering said collagen hydrolysate in a tablet.

3. The method of claim 1, wherein said oral administration is conducted by administering said collagen hydrolysate in a capsule.

4. The method of claim 1, wherein said oral administration is conducted by administering said collagen hydrolysate in a food product.

5. The method of claim 1, wherein said oral administration is conducted by administering said collagen hydrolysate in a drink.

6. The method of claim 1, wherein said collagen hydrolysate has been obtained from bovine collagen.

7. The method of claim 1, wherein said collagen hydrolysate has been obtained from porcine collagen.

8. The method of claim 1, wherein said collagen hydrolysate has been obtained from chicken collagen.

9. The method of claim 1, wherein said collagen hydrolysate has been obtained from fish collagen.

10. The method of claim 1, wherein said oral administration is conducted by administering said collagen hydrolysate in an amount of about 10 grams per day.

11. The method of claim 10, wherein said oral administration is conducted by administering said collagen hydrolysate for at least one week.

12. The method of claim 1, wherein said oral administration is conducted by administering said collagen hydrolysate for at least one week.

\* \* \* \* \*